United States Patent
Putsherry et al.

(12) 
(10) Patent No.: US 9,261,490 B2
(45) Date of Patent: Feb. 16, 2016

(54) ULTRASONIC TRANSDUCER ARRANGEMENT

(75) Inventors: Dinesh Damodar Putsherry, Mumbai (IN); Abraham Kurian, Pathanamthitta District (IN); Jayadev Muraleedhara Panicker, Alapuzha District (IN)

(73) Assignee: J. RAY MCDERMOTT, S.A., Houston, TX (US)

( * ) Notice: Subject to any disclaimer, the term of this patent is extended or adjusted under 35 U.S.C. 154(b) by 447 days.

(21) Appl. No.: 13/433,450

(22) Filed: Mar. 29, 2012

(65) Prior Publication Data

US 2013/0255384 A1 Oct. 3, 2013

(51) Int. Cl.
*G01N 29/04* (2006.01)
*G01N 29/26* (2006.01)
*G01N 29/06* (2006.01)
*G01N 29/265* (2006.01)

(52) U.S. Cl.
CPC ............ *G01N 29/262* (2013.01); *G01N 29/069* (2013.01); *G01N 29/265* (2013.01); *G01N 2291/106* (2013.01); *G01N 2291/267* (2013.01); *G01N 2291/2634* (2013.01)

(58) Field of Classification Search
CPC .............. G01N 29/069; G01N 29/265; G01N 2291/267
USPC .......................................... 73/588, 598, 622
See application file for complete search history.

(56) References Cited

U.S. PATENT DOCUMENTS

| 3,580,057 | A | * | 5/1971 | Seegmiller | ............ E21F 17/185 310/328 |
| 7,168,322 | B2 | * | 1/2007 | Bardoux et al. | ................. 73/588 |
| 7,762,137 | B2 | * | 7/2010 | van der Ent et al. | ............ 73/627 |
| 2009/0114021 | A1 | * | 5/2009 | den Boer | ........................ 73/596 |

FOREIGN PATENT DOCUMENTS

| CN | 101256173 A | 9/2008 |
| CN | 101368932 A | 2/2009 |
| CN | 201397319 Y | 2/2010 |
| CN | 201607430 U | 10/2010 |
| ES | 2302615 A1 | 7/2008 |
| JP | 8-201350 | 8/1996 |
| JP | 2001-050938 A | 2/2001 |

OTHER PUBLICATIONS

Chinese Office Action dated Jan. 12, 2015 for Application No. 201310070011.2 (MCDR/0032CN).
Mexican Office Action dated Aug. 27, 2015 for Application No. MX/a/2012/015117.

* cited by examiner

*Primary Examiner* — John Chapman, Jr.
(74) *Attorney, Agent, or Firm* — Patterson & Sheridan, LLP

(57) ABSTRACT

An ultrasonic transducer arrangement for inspecting a pipe to fitting weld with restricted scanning access. A TOFD ultrasonic send transducer is mounted adjacent one end of a frame. A TOFD ultrasonic receive transducer is mounted on the frame and spaced linearly apart from and aligned with the TOFD send transducer. The TOFD send and receive transducers are each positioned at an angle that matches the external radius of curvature of the pipe. A phased array curved, wedge, send/receive transducer is mounted on the frame and spaced radially apart from the TOFD transducers.

10 Claims, 3 Drawing Sheets

ULTRASONIC TRANSDUCER ARRANGEMENT

FIELD AND BACKGROUND OF INVENTION

The invention is generally related to the inspection of welds and, more particularly, to the ultrasonic inspection of pipe-to-fitting welds where there is limited clearance.

In the offshore drilling industry for producing oil and natural gas, production, delivery, and various processes on the offshore rigs and platforms require the use of a variety of pipes and fittings that must be welded together. Safety requirements require that the welds be inspected for the detection and repair of weld defects.

Previously, radiography was the primary method of inspection for process piping welds with limited clearance for inspection. The non-destructive inspection of carbon steel pipe-to-fitting joints using the alternative method of ultrasonic inspection is preferred.

A limitation of ultrasonic inspection is that ultrasonic transducers must be able to be positioned on the parent material adjacent to the weld so as to satisfactorily inspect the full volume of the weld. As seen in FIG. 1, using phased array ultrasonic transducers 40 to inspect the weld 42 between straight sections of pipe 44 or curved sections of pipe presents no issues as long as the radius of the curvature at a pipe bend is not so small as to prevent proper positioning of the transducers. Typically, about 110 mm of scanning access is required on both sides of the weld for an adequate inspection of the full weld volume.

As seen in FIGS. 2 and 3, production and process piping requires that fittings 43 for valves, controls, gauges, manifolds, or curved pipes, etc. be included in the pipes 44. Ultrasonic inspection of pipe-to-fitting welds 42 can present a challenge due to the smaller radius of curvature at the fitting and restricted scanning access on the fitting side of the weld. An example is indicated as area 46 in FIG. 2, which can make it difficult or impossible to inspect the full volume of the weld with previous transducer arrangements. A result is that a blind area 48 such as that indicated in FIG. 3 may exist where the ultrasonic transducers are not capable of being properly positioned for inspecting the full area of the weld 42.

Phased array ultrasonic inspection of pipe-to-fitting welds from the pipe side of the weld typically does not detect defects on the fitting side of the weld. It can be seen from the above that there is a need for an improved ultrasonic transducer arrangement for inspecting the fitting side of pipe-to-fitting welds.

SUMMARY OF INVENTION

The present invention is drawn to an ultrasonic transducer arrangement for inspecting pipe-to-fitting welds. The invention generally comprises a phased array, curved wedge send/receive transducer mounted on a frame, a time of flight diffraction (TOFD) ultrasonic send transducer mounted adjacent one end of the frame and spaced linearly and radially apart from the phased array transducer, and a TOFD ultrasonic receive transducer mounted on the frame and spaced linearly apart from and aligned with the TOFD send transducer. The send and receive transducers are each positioned at an angle that matches the external radius of curvature of the pipe.

The various features of novelty which characterize the invention are pointed out with particularity in the claims annexed to and forming part of this disclosure. For a better understanding of the present invention, and the operating advantages attained by its use, reference is made to the accompanying drawings and descriptive matter, forming a part of this disclosure, in which a preferred embodiment of the invention is illustrated.

BRIEF DESCRIPTION OF THE DRAWINGS

In the accompanying drawings, forming a part of this specification, and in which reference numerals shown in the drawings designate like or corresponding parts throughout the same.

DESCRIPTION OF THE PREFERRED EMBODIMENTS

Figure 7:
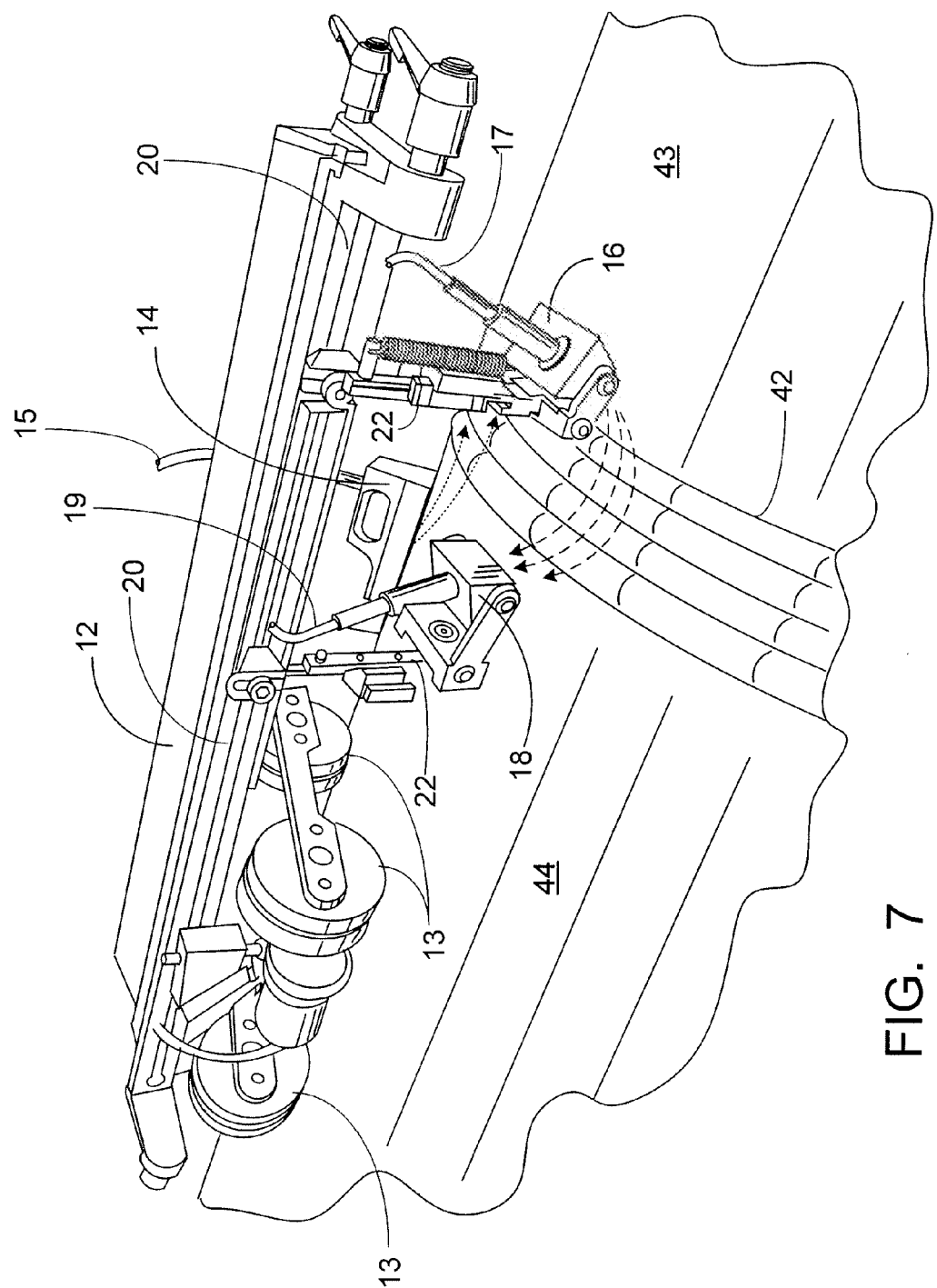
FIG. 7 is a perspective view of the invention.

As seen in FIG. 7, the ultrasonic transducer arrangement 10 is generally comprised of a frame 12, a phased array transducer 14, a send transducer 16, and a receive transducer 18.

The frame 12 is made from any suitable material such as aluminum or steel and is provided with wheels 13 for moving the frame and transducers around the pipe 44 during the inspection process. The wheels 13 may be magnetic for holding the assembly on the pipe 44. The frame 12 may be provided with means for adjusting the spacing between transducers, such as channels 20 for receiving the transducer mounts 22.

The phased array transducer 14 is preferably a curved wedge send/receive transducer. A cable 15 is attached between the transducer 14 and an electronic sending/receiving unit (not shown) that provides the electrical current to generate the ultrasonic pulse and then receives and records the reflected pulse (signal) sensed by the phased array transducer 14. The phased array transducer 14 is positioned to insure that the face of the transducer that sends and receives the ultrasonic pulses is at the proper angle for sending the ultrasonic pulse into the weld 42. Send/receive transducers are known in the industry and designed to send an ultrasonic signal or pulse into a work piece such as a pipe and/or weld and receive the reflected signal for recording and analyzing the condition of the pipe or a weld between two pipes or between a pipe and a fitting. The recorded, reflected signals are analyzed to determine the presence, location, and depth of defects in the pipe wall and/or weld.

The send transducer 16 is preferably a time of flight diffraction (TOFD) transducer. This transducer 16 is spaced radially and linearly apart from the phased array transducer 14 such that the send transducer 16 is on the fitting side of the weld 42 during inspection and the phased array transducer 14 is on the pipe side of the weld 42 during the inspection. Thus, radial spacing is meant to refer to spacing apart around the circumference of the pipe 44 and linear spacing is meant to refer to spacing apart along the longitudinal axis of the pipe 44. A cable 17 is attached between the transducer 16 and the electronic sending/receiving unit referenced above that is used for generating the ultrasonic pulse in the transducer 16.

The receive transducer 18 is preferably a time of flight diffraction (TOFD) transducer. This transducer 18 is linearly spaced apart from the send transducer 16 such that the receive transducer 18 is on the pipe side of the weld 42 during the inspection. A cable 19 is attached between the transducer 18 and the electronic sending/receiving unit referenced above for receiving the reflected ultrasonic pulse sensed by the receive transducer 18.

Both TOFD transducers 16 and 18 are preferably wedge shaped to have a narrow contact footprint that is readily accommodated on the fitting side of the weld 42. Also, the TOFD send and receive transducers 16 and 18 are positioned to be angled toward each other for efficiently sending and sensing the ultrasonic pulses.

For ease of illustration, any additional equipment known in the industry such as means for coupling the transducers is not shown.

It should be understood that, in some instances, there may be continuing welding operations in the vicinity of the weld being inspected. The electrical fields generated by such nearby welding operations may cause interference with the transducers during their operation. To eliminate this interference, a non-conductive material that does not affect the sending or receiving of the ultrasonic pulses, such as a polystyrene plastic, may be used to encase the transducers. One example of such a material is Rexolite® plastic made by C-Lec Plastics, Inc.

Figure 2:
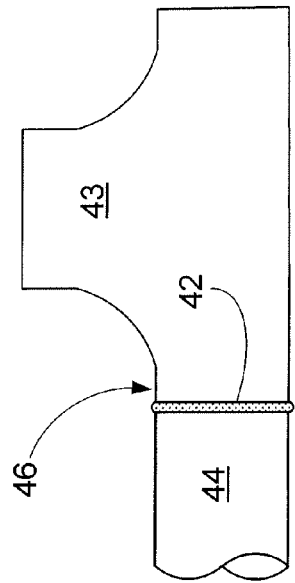
FIG. 2 is an elevation view that indicates the area of limited access for inspecting a pipe to fitting weld.
Figure 4:
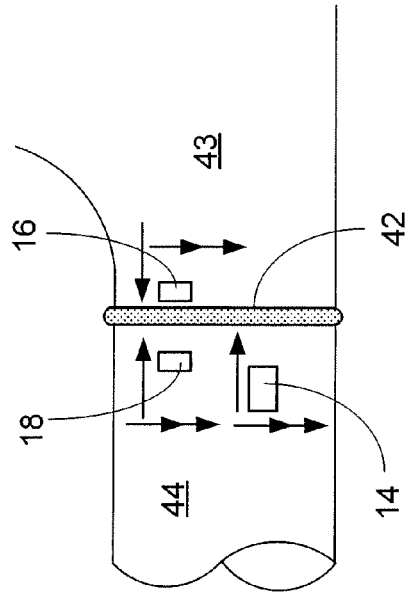
FIG. 4 is a schematic view of the invention that illustrates the relative positioning of the transducers.
Figure 1:
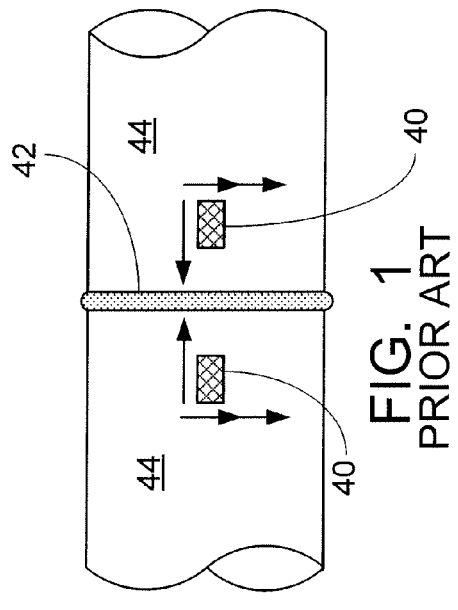
FIG. 1 illustrates the prior art for inspecting a pipe to pipe weld.

In operation, as seen in FIGS. 4 and 7, the frame 12 is placed on a pipe 44 such that the phased array transducer 14 is positioned adjacent the weld 42 on the pipe side of the weld 42, the send transducer 16 is positioned adjacent the weld 42 on the fitting side of the weld 42, and the receive transducer 18 is positioned adjacent the weld 42 on the pipe side of the weld 42 and aligned with the send transducer 16. For ease of illustration and explanation, the path of the ultrasonic pulses from the TOFD send transducer 16 and the phased array transducer 14 are shown in separate drawings, FIGS. 5 and 6 respectively.

Figure 6:
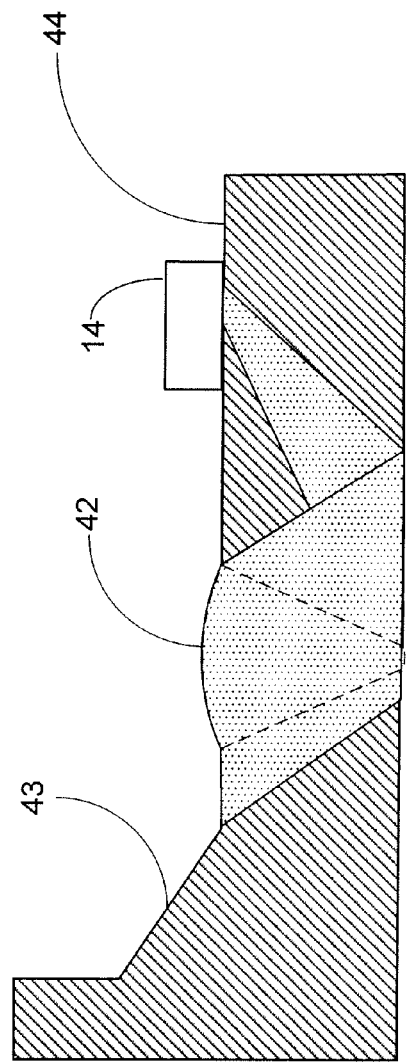
FIG. 6 illustrates the path of the ultrasonic pulse from the phased array transducer.

The transducers 14 and 16 are caused to generate an ultrasonic pulse into the weld 42, fitting 43, and pipe 44. FIG. 6 illustrates the path of the ultrasonic pulse from the phased array transducer 14 through the pipe wall and weld material. It can be seen that the ultrasonic pulse travels from the phased array transducer 14 into the pipe wall, reflects off the inner wall of the pipe 44 toward and through the weld 42 and the outer wall of the fitting 43 on the fitting side of the weld 42, and then reflects back toward the phased array transducer 14. The phased array transducer 14 receives the ultrasonic pulse that travels from the transducer 14, through the weld 42 and pipe 44, and is then reflected back from the pipe walls or defects to the phased array transducer 14.

Figure 5:
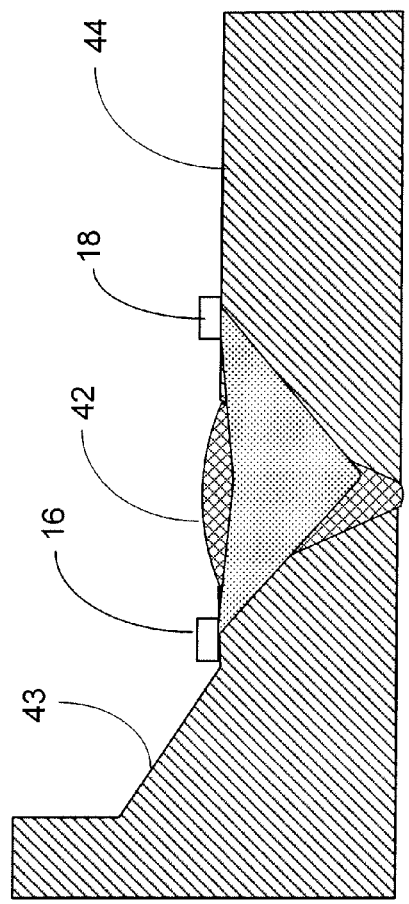
FIG. 5 illustrates the path of the ultrasonic pulse from the TOFD send transducer.

As seen in FIG. 5, the ultrasonic pulse from the TOFD send transducer 16 travels through the outer wall of the fitting 43 and the weld 42 and reflects off the wall of the pipe 44 at the weld interface. The TOFD receive transducer 18 receives the ultrasonic pulse from the TOFD send transducer 16 that travels through the weld 42 and pipe 44. The electronic equipment used to send the electrical signals to the transducers 14 and 16 for generating the ultrasonic pulses also receives and records the reflected pulses sensed by the transducers 14 and 18. Analysis of the results as known in the industry is accomplished as briefly described below.

The frame 12 and transducers 14, 16, and 18 are rotated around the pipe as indicated by the double arrows in FIG. 4 to inspect the entire circumference of the weld 42 around the pipe 44 and fitting 43. The sending and receiving of ultrasonic pulses, and recording of the results, is continued as the frame 12 and transducers 14, 16, and 18 are rotated around the pipe to insure inspection of the entire circumference of the weld.

Hardware and software known in the industry, connected to the transducers via cables 15, 17, and 19, is used to collect, store, and read the testing results (timing of sent ultrasonic pulses and received, reflected ultrasonic pulses) to determine the existence, location, and depth of any defects that may be present in the weld.

Figure 3:
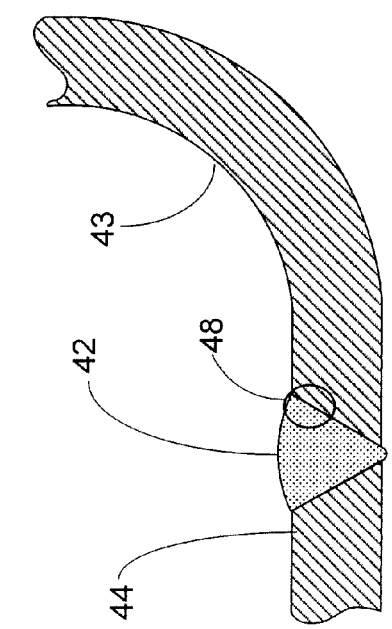
FIG. 3 is a section view that illustrates the pipe and fitting wall, the weld between them, and the typical blind area that ultrasonic inspection cannot inspect when presented with restricted access.

It is seen that the inventive concept achieves inspection of the full volume of the weld 42 by using the phased array transducer 14 to send an ultrasonic pulse from the pipe side of the weld 42 and inspect the pipe side of the weld 42 and the lower bevel area on the fitting side of the weld 42. The TOFD transducers 16 and 18 are essentially focused to inspect the fitting side of the weld (the blind area 48 shown in FIG. 3 where defects on the bevel are missed by the phased array probe). This eliminates the blind area 48 indicated in FIG. 3 that a single phased array transducer cannot inspect due to space restrictions on the fitting side of the weld 42 at the portion of the fitting that extends at an angle to the pipe 44 and causes the restricted access. This is different from the prior art which required a phased array transducer on both sides of the weld in order to inspect the full volume of the weld.

The invention provides several advantages.

Only 12 mm of scanning access is required on the fitting side of the weld as opposed to the 110 mm required in the prior art.

There is no radiation hazard as is present during the use of radiography. Thus, surrounding activities are not affected and work in the vicinity of the weld being inspected may be continued without down time.

Ultrasonic inspection typically requires only one fifth the time of radiographic inspection.

Ultrasonic inspection provides immediate results whereas radiographic inspection results are not.

Inspection data can be archived on compact disk or a hard drive.

Ultrasonic inspection requires no consumables.

The inspection is more sensitive than previously used methods for pipe-to-fitting welds and is capable of detecting all types of defects.

The height, width, and depth of defects can be measured.

The entire circumference of the weld can be inspected using the invention, including the area of restricted access at a fitting.

While specific embodiments and/or details of the invention have been shown and described above to illustrate the application of the principles of the invention, it is understood that this invention may be embodied as more fully described in the claims, or as otherwise known by those skilled in the art (including any and all equivalents), without departing from such principles.

What is claimed as invention is:

1. An ultrasonic transducer arrangement for inspecting a pipe to fitting weld where scanning is restricted on the fitting side, comprising:
   a. a frame;
   b. a first transducer being a phased array curved wedge ultrasonic, send/receive transducer mounted on the frame;
   c. a second transducer being an ultrasonic, send transducer mounted adjacent one end of the frame and spaced linearly and radially apart from the phased array wedge transducer; and d. a third transducer being an ultrasonic, receive transducer mounted on the frame spaced linearly apart from and aligned with the send transducer to receive signals from the send transducer, the third transducer being wedge shaped and having a narrow end and a wide end opposite the narrow end, wherein the narrow end of the third transducer is angled toward the second transducer.

2. The transducer arrangement of claim 1, wherein the second and third transducers are time of flight transducers.

3. The transducer arrangement of claim 1, wherein the first transducer has a curved face that matches the external curvature of the pipe.

4. The transducer arrangement of claim 1, further comprising wheels coupled to the frame.

5. The transducer arrangement of claim 4, wherein the second transducer is wedge shaped and has a narrow end and a wide end opposite the narrow end, and wherein the narrow end of the second transducer is angled toward the third transducer.

6. The transducer arrangement of claim 5, wherein the wheels are magnetic.

7. An ultrasonic transducer arrangement for inspecting a pipe to fitting weld where scanning is restricted on the fitting side, comprising:
  a. a frame;
  b. a first transducer being a phased array curved wedge ultrasonic, send/receive transducer mounted on the frame, the first transducer having a curved face that matches the external curvature of the pipe;
  c. a second transducer being a wedge ultrasonic, time of flight diffraction, send transducer mounted on the frame spaced linearly and radially apart from the first transducer, the second transducer being wedge shaped and having a narrow end and a wide end opposite the narrow end; and
  d. a third transducer being a wedge ultrasonic, time of flight diffraction, receive transducer mounted on the frame spaced linearly apart from and aligned with the second transducer to receive signals from the second transducer, the third transducer being wedge shaped and having a narrow end and a wide end opposite the narrow end, wherein the narrow end of the third transducer and the narrow end of the second transducer are angled toward one another.

8. A method for inspecting the fitting side of a pipe-to-pipe fitting weld where scanning is restricted on the fitting side, comprising:
  a. positioning a first transducer being a phased array curved wedge ultrasonic, send/receive transducer adjacent the weld on the pipe side of the weld;
  b. positioning a second transducer being a wedge ultrasonic, send transducer on the fitting side of the weld with scanning restriction and radially spaced apart from the first transducer, the second transducer being wedge shaped and having a narrow end and a wide end opposite the narrow end;
  c. positioning a third transducer being a wedge ultrasonic, receive transducer on the pipe side of the weld and aligned with the second transducer to receive signals from the second transducer, wherein the third transducer is wedge shaped and has a narrow end and a wide end opposite the narrow end, wherein the narrow end of the third transducer and the narrow end of the second transducer are angled toward one another;
  d. activating the first transducer and the second transducer to send an ultrasonic pulse into the pipe and weld material;
  e. receiving the reflected ultrasonic signal sent by the first transducer with the first transducer and the reflected/diffracted ultrasonic signal sent by the second transducer with the third transducer; and
  f. storing and processing the reflected ultrasonic signals to determine the presence and location of defects in the weld.

9. The method of claim 8, wherein the second and third transducers are time of flight diffraction transducers.

10. The method of claim 8, wherein the first transducer has a curved face that matches the external curvature of the pipe.

* * * * *